United States Patent

Annis et al.

[11] Patent Number: 5,869,657
[45] Date of Patent: Feb. 9, 1999

[54] PREPARATION OF ARTHROPODICIDAL OXADIAZINES

[75] Inventors: Gary David Annis, Landenberg, Pa.; Stephen Frederick McCann, Newark; Rafael Shapiro, Wilmington, both of Del.

[73] Assignee: E. I. du Pont de Nemours and Company, Wilmington, Del.

[21] Appl. No.: 727,607

[22] Filed: Oct. 16, 1996

Related U.S. Application Data

[63] Continuation-in-part of Ser. No. 230,568, Apr. 20, 1994, abandoned, which is a continuation-in-part of Ser. No. 298,909, Aug. 31, 1994, abandoned.

[51] Int. Cl.⁶ .................................................. C07D 273/04
[52] U.S. Cl. ................................................. 544/66; 560/28
[58] Field of Search .................................................. 544/66

[56] References Cited

U.S. PATENT DOCUMENTS

| | | | |
|---|---|---|---|
| 3,755,453 | 8/1973 | Rosenthal et al. | 260/586 |
| 3,950,367 | 4/1976 | Botta | 260/455 |
| 4,489,074 | 12/1984 | Brown et al. | 424/246 |

FOREIGN PATENT DOCUMENTS

| | | |
|---|---|---|
| 0192150 | 8/1986 | European Pat. Off. . |
| 129624 | 4/1986 | Poland . |
| WO 92/11249 | 7/1992 | WIPO . |
| WO 92/20682 | 11/1992 | WIPO . |

OTHER PUBLICATIONS

Masui et al, New Methods and Reagents in Organic Synthesis. 75., *Tetrahedron Letters*, vol. 29, No., 23, 2835–2838, 1988.

Padwa et al., Involvement of Enol Tautomers in the Photoisomerization of 3–Substituted Isochromanones, *Journal of the American Chemical Society*, vol. 98, No. 18, 5581–5590, 1976.

T. Girija et al, Synthetic Investigations on Illudinine: a new synthesis of methyl 8–methoxy–2,2–dimethyl–7–oxo–1,2,3, 5,6,7–hexahydro–s–indacene–4–carboxylate, *Journal of the Chemical Society*, No. 6, 1467–1471, Jun., 1991.

Schulze, W. *Chemical Abstract*, Abstract No. 112:179779, with the reaction involving 126280–47–5 and 110–91–8 as searched in CASREACT (1989).

*Primary Examiner*—Richard L. Raymond

[57] ABSTRACT

A method for making arthropodicidal oxadiazines and intermediates which are racemic or enantiomerically enriched at their chiral center, the method for making the oxadiazines comprising reaction of an intermediate selected from

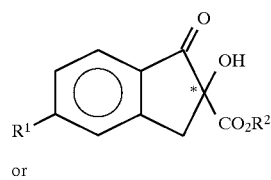

or

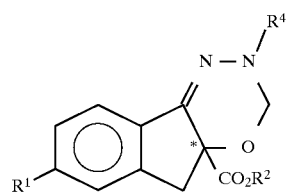

wherein:

$R^1$ is F, Cl, or $C_1$–$C_3$ fluroalkoxy, $R^2$ is $C_1$–$C_3$ alkyl, and $R^4$ is H or $CO_2CH_2(C_6H_5)$.

as well as certain selected intermediates including those depicted above, and methods of making them.

6 Claims, No Drawings

PREPARATION OF ARTHROPODICIDAL OXADIAZINES

CROSS-REFERENCE TO RELATED APPLICATIONS

This application claims priority benefit under 35 U.S.C. 371 from PCT/US95/04321 filed Apr. 17, 1995, which is, in-turn, a continuation-in-part application of application Ser. No. 08/230,568 filed Apr. 20, 1994, now abandoned, and application Ser. No. 08/298,909 filed Aug. 31, 1994, now abandoned.

BACKGROUND OF THE INVENTION

The present invention pertains to the preparation of arthropodicidal oxadiazines and intermediates therefor.

Arthropodicidal oxadiazines are disclosed in WO 9211249 and WO 9319045. However, preparative methods for these compounds must be improved for economic commercial operation. Accordingly, the present invention provides a convenient route to preferred arthropodicidal oxadiazines.

SUMMARY OF THE INVENTION

The present invention pertains to a process for preparing a compound of Formula I which is racemic or enantiomerically enriched at chiral center *

[Structure of Formula I]

wherein $R^1$ is F, Cl, or $C_1$–$C_3$ fluoroalkoxy, and $R^2$ is $C^1$–$C_3$ alkyl, comprising:

(a) reacting a compound of Formula II, optionally enantiomerically enriched at *,

[Structure of Formula II]

with the compound of Formula III in the presence of an acid catalyst $$H_2N-NHR^3 \qquad III$$

to form a compound of Formula IV

[Structure of Formula IV]

wherein $R^3$ is a protecting group such as $CO_2CH_2(C_6H_5)$ and the like;

(b) reacting the compound of Formula IV with di($C_1$–$C_3$ alkoxy)methane in the presence of a Lewis acid to form a compound of Formula V

[Structure of Formula V]

(c) hydrogenating the compound of Formula V to form a compound of Formula VI

[Structure of Formula VI] and (d) reacting the compound of Formula VI with the compound of Formula VII

[Structure of Formula VII]

to form a compound of Formula I having substantially the same absolute configuration as the compound of Formula II.

The present invention further pertains to a process for preparing a compound of Formula I enantiomerically enriched at chiral center * comprising Steps a–d wherein the compound of Formula II in Step a is enantiomerically enriched at * with the same configuration as the desired compound of Formula I.

The present invention further pertains a process for preparing a compound of Formula I enantiomerically enriched at chiral center * comprising Steps a–d and further comprising (i) reacting para-substituted phenylacetyl halide with ethylene in the presence of Lewis acid to produce compounds of Formula VIII

[Structure of Formula VIII]

(ii) reacting VIII with peroxyacid to produce compounds of Formula IX

[Structure of Formula IX]

(iii) reacting IX with $C_1$–$C_3$ alcohol in the presence of acid catalyst to produce compounds of Formula X

[Structure of Formula X]

(iv) reacting X with base to produce compounds of Formula XI

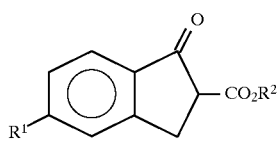

and (v) reacting XI with hydroperoxide in the presence of chiral base to produce enantiomerically enriched II;

wherein enantiomerically enriched II from step v is reacted in step a and wherein $R^1$ and $R^2$ are as previously defined.

The present invention further pertains to the individual process steps a, b, c and d and to multi-step processes a, b; a, b, c; b, c; b, c, d; and c, d.

The present invention further pertains to the single process step v for preparing enantiomers of Formula II from compounds of Formula XI; the five-step i–v process to prepare compounds of Formula II; the four-step i–iv process for the preparation of compounds of Formula XI from para-substituted phenylacetyl halide; the two-step i–ii process to prepare compounds of Formula IX; the single process step ii to prepare compounds of Formula IX; and, the two-step ii–iii process to prepare compounds of Formula X.

The present invention further pertains to (+) enantiomers of compounds of Formula II:

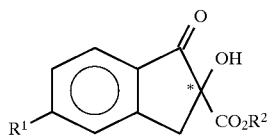

wherein $R^1$ is selected from the group F, Cl and $C_1$–$C_3$ fluoroalkoxy, and $R^2$ is $C_1$–$C_3$ alkyl, which compounds are substantially pure (+) enantiomers.

The present invention further pertains to racemic and enantiomerically enriched compounds of Formulae IV, V and VI:

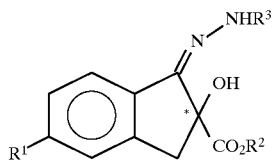

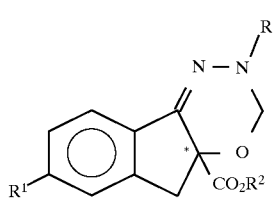

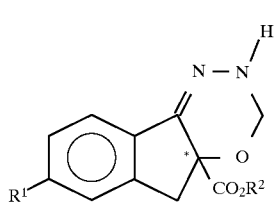

wherein $R^1$ is F, Cl, or $C_1$–$C_3$ fluoroalkoxy, $R^2$ is $C_1$–C3 alkyl, and $R^3$ is $CO_2CH_2(C_6H_5)$.

The present invention further pertains to the compound of Formula VII.

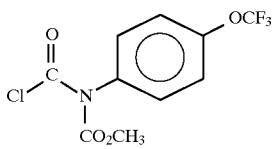

The present invention further pertains to compounds of Formulae IX and X

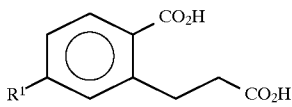

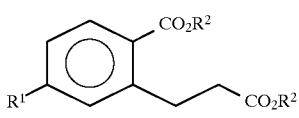

wherein $R^1$ is selected from the group F, Cl and $C_1$–$C_3$ fluoroalkoxy, and $R^2$ is $C_1$–$C_3$ alkyl.

In the above definitions, the term "halide" means fluoride, chloride, bromide or iodide. The term "$C_1$–$C_3$ alkyl" indicates straight chain or branched alkyl with 1, 2 or 3 carbon atoms and means methyl, ethyl, n-propyl or isopropyl. The term "$C_1$–$C_3$ alkoxy" means methoxy, ethoxy, n-propoxy or isopropoxy. The term "$C_1$–$C_3$ fluoroalkoxy" means methoxy, ethoxy, n-propoxy or isopropoxy partially or fully substituted with fluorine atoms and includes, for example, $CF_3O$ and $CF_3CH_2O$. The term "$C_1$–$C_3$ alcohol" means methyl, ethyl, n-propyl or isopropyl alcohol.

Preferred compounds of Formulae IV, V and VI are those where $R^2$ is methyl and $R^1$ is chlorine, $CF_3O$ or $CF_3CH_2O$. Most preferred are phenylmethyl[5-chloro-2,3-dihydro-2-hydroxy-2-(methoxycarbonyl)-1H-inden-1-ylidene] hydrazinecarboxylate (designated IVa);

4a-methyl 2-(phenylmethyl)-7-chloroindeno [1,2-e] [1,3,4] oxadiazine-2,4a(3H, 5H)-dicarboxylate (designated Va); and methyl 7-chloro-2,5-dihydroindeno[ 1,2-e] [1,3,4] oxadiazine-4a(3H)-carboxylate (designated VIa).

Preferred compounds of Formulae II, IX and X are those wherein $R^2$ is methyl and $R^1$ is chlorine, bromine, $CF_3O$ or $CF_3CH_2O$. Most preferred are (+)methyl 5-chioro-1,3-dihydro-2-hydroxy-1-oxo-2H-indene-2-carboxylate (designated (+)IIa);

2-carboxy-5-chlorobenzenepropanoic acid (designated IXa); and methyl 5-chloro-2-(methoxycarbonyl)benzenepropanoate (designated Xa).

DETAILED DESCRIPTION OF THE INVENTION

One aspect of this invention pertains to a process for preparing compounds of Formula I comprising four steps, a-d, typically operated as follows.

Step a) forms IV by reacting II (prepared for example from substituted indanone, such as 5-chloro-1-indanone, as described in detail in WO 9211249) with about a molar equivalent of III in the presence of acid catalyst such as p-toluenesulfonic, sulfuric or acetic acid, optionally in an inert solvent such as methanol, isopropanol, tetrahydrofluran, dichloromethane, 1,2-dichloroethane and the like. Typical reaction conditions include temperatures of about 40° to 120° C., preferably 65° to 85° C., for about 0.5 to 25 h. Compound IV can be recovered by standard methods such as filtration, optionally after dilution of the reaction mixture with water. Alternatively, IV can be extracted with solvent and used directly in the next reaction step without isolation.

Step b) forms V by reacting IV with di($C_1$–$C_3$ alkoxy) methane such as dimethoxymethane or diethoxymethane in the presence of a Lewis acid, optionally in an inert solvent such as dichloromethane, 1,2-dichloroethane, chlorobenzene, α,α, α-trifluorotoluene and the like. The di($C_1$–$C_3$ alkoxy)methane can be in molar excess. Lewis acids include $P_2O_5$, $BF_3$ and $SO_3$, which generally require 0.9 to 4.0 molar equivalents (relative to V) for best results; further included are metal (especially scandium, ytterbium, yttrium and zinc) trifluoromethanesulfonates, which can be used in about 0.1 to 0.5 molar equivalents relative to V. The most preferred Lewis acids for this step are $P_2O_5$ and SO3; the SO3 may be in the form of a complex such as DMF.SO3 (DMF is dimethylformamide). Typical reaction conditions include temperatures of about 20° to 150° C., preferably 50° to 60° C., and pressures of about 100 to 700 kPa, preferably 100 to 300 kPa, for about 0.5 to 48 h. It is preferable to continuously remove the byproduct $C_1$–$C_3$ alcohol by distillation during the reaction when non-sacrificial Lewis acid such as a rare-earth trifluoromethanesulfonate is employed. Compound V can be recovered by standard methods such as filtration and used without further purification in the next reaction step. Alternatively, when metal trifluoromethanesulfonates are employed as the Lewis acid, V can be recovered by concentrating the reaction mass, optionally diluting with an inert, water-immiscible solvent such as ethyl acetate, washing with water to remove the metal trifluoromethanesulfonates, concentrating the organic phase and inducing V to crystallize from same, optionally by adding a suitable solvent such as aqueous methanol, hexane and the like.

Step c) forms VI by reacting V with hydrogen, from a hydrogen source or preferably molecular hydrogen itself, in the presence of a hydrogenolysis metal catalyst such as palladium, preferably supported on a substance such as charcoal, in an inert solvent such as methyl acetate, ethyl acetate, toluene, diethoxymethane or $C_1$–$C_3$ alcohol. Typical reaction conditions include temperatures of about 0° to 30° C., preferably about 20° C. and pressures of about 105 to 140 kPa, preferably about 35 kPa, for about 3 h. Compound VI can be recovered from solution by standard methods such as filtering and collecting the palladium for recycle to subsequent batches, separating the organic phase, concentrating same by removing solvent and inducing crystallization of VI, optionally by adding aqueous $C_1$–$C_3$ alcohol, acetonitrile or aliphatic hydrocarbon such as hexane. Preferably compound VI is used in the next step without isolation from solution in the organic phase.

Step d) forms I by reacting VI with about a molar equivalent of VII optionally in the presence of about 1.0 to 1.5 molar equivalents (relative to VII) of an acid scavenger such as trialkylamine, pyridine or, preferably, aqueous sodium carbonate or bicarbonate, in an inert solvent such as toluene, xylene, methyl acetate, ethyl acetate, dichloromethane, 1,2-dichloroethane, diethoxymethane and the like. Typical reaction conditions include temperatures of about 0° to 30° C. for about 0.2 to 2 h. Compound I can be recovered by standard methods such as washing the reaction mixture with aqueous acid or aqueous sodium chloride, concentrating the organic phase and inducing crystallization of I from same, optionally by addition of a $C_1$–$C_3$ alcohol, water, alcohol-water mixtures or an aliphatic hydrocarbon such as hexane. Steps c and d can be combined in a single reaction pot by adding VII and the optional acid scavenger during the hydrogenolysis of V. In this way, compound VI is acylated as soon as it is formed to give I. Typical solvents for the combined steps c and d are methyl acetate, ethyl acetate, toluene, xylene, dichloromethane, 1,2-dichloroethane and the like. Acid scavengers can be a trialkylamine such as tripropylamine, tributylamine, diisopropylethylamine, and the like, or a solid inorganic compound such as sodium bicarbonate, calcium oxide, sodium pyrophosphate, citric acid trisodium salt and the like.

Reactions steps a-d proceed substantially with retention of configuration at chiral center *. In a preferred embodiment, the compound of Formula II employed in step a is enantiomerically enriched thereby providing a compound of Formula I which is enantiomerically enriched with the same absolute configuration. By enantiomerically enriched it is meant that a bulk sample of the compound contains an excess of either the (+) or (−) enantiomer and includes anything greater than a 1-to-1(racemic) mixture of enantiomers up to and including 100% of the pure enantiomer. Thus, for example, an enriched compound having 25% (−) enantiomer and 75% (+) enantiomer is viewed as a mixture of 50% racemate and 50% pure (+) enantiomer and is referred to as having 50% enantiomeric excess of the (+) enantiomer. In an especially preferred embodiment of the present invention, the compound of Formula II is enriched with the (+) enantiomer which leads to a compound of Formula I enriched with the (+) enantiomer, the (+) enantiomer having been found to be the more arthropodicidally active enantiomer.

Enrichment of the compound of Formula II is preferably at least 10% and more preferably at least 20% of the (+) enantiomer.

Enantiomerically enriched compounds of Formula II can be produced, for example, by physically separating the enantiomers of a racemic mixture according to standard methods. However, such methods are difficult to operate on a large scale and are often wasteful as the undesired enantiomer must be discarded. In a preferred embodiment of the present invention, an enantiomerically enriched compound of Formula II is prepared by an enantioselective process comprising five steps, i–v. By "enantioselective" is meant that the desired enantiomer of the chiral product is formed preferentially, although not necessarily exclusively. Steps i–v are typically operated as follows.

Step i) forms VIII by reacting an appropriately-substituted phenylacetyl halide which can be purchased (for example from Spectrum Chemical Manufacturing Co.) or prepared from the acids by known procedures and optionally generated in situ, with about 1to 4 molar equivalents, preferably 2 molar equivalents, of ethylene gas and about 0.9 to 1.5 molar equivalents of a Lewis acid such as aluminum chloride in about 3 to 10 parts by weight of an inert solvent such as dichloromethane, dichloroethane, carbon disulfide, or o-dichlorobenzene. Typical reaction conditions include temperatures in the range of about −20° to +30° C., preferably −5° to 0° C., pressures in the range of about 60 to 400 kPa and reaction times of about 0.5 to 8 h. Compound VIII can be isolated by standard methods or when the solvent is suitable, for example dichloromethane or dichloroethane, the reaction mixture can be employed in the next step without isolation of VIII. In a preferred embodiment, the reaction mixture from Step i is employed in Step ii without isolation of VIII.

Step ii) forms IX by reacting VIII with about 2.5 to 3.5 equivalents of a peroxycarboxylic acid, preferably peroxyacetic acid, in an inert solvent such as acetic acid, dichloromethane, o-dichlorobenzene, or 1,2-dichloroethane. Typical reaction conditions include temperatures in the range of about 15° to 55° C., preferably 25° to 45° C., and reaction times of about 5 to 35 h. The temperature is kept low for safety reasons. Preferably, but not necessarily, the reaction is conducted in the presence of 0.5 to 2.5 molar equivalents of a buffering agent such as sodium acetate. The rate of addition of the peroxycarboxylic acid to the solution of VIII is controlled to avoid accumulating excess peroxycarboxylic acid. The product can be isolated, for example, by quenching with water, optionally adding a reducing agent such as sulfur dioxide to remove excess oxidant, and filtering. If necessary, the pH can be adjusted below 3 before filtration of the product.

Step iii) forms X by esterification of IX according to standard methods. In a preferred embodiment, IX is reacted with alcohol solvent (about 2 to 20 parts by weight) in the presence of about 1 to 20 molar equivalents of the corresponding carbonate derivative of the alcohol as a dehydrating agent and about 0.001 to 0.2 molar equivalents of an acid catalyst, such as sulfuric acid or p-toluenesulfonic acid; wherein typical reaction conditions include temperatures in the range of about 75° to 105° C., pressures in the range of about 100 to 500 kPa and reaction times of about 10 to 30 hours. Compound X can be isolated by standard methods. Alternatively, the reaction mixture can be employed in the next step without isolation of X. Preferably, X is not isolated before Step iv.

Step iv) forms XI by reacting X with a strong base such as an alkali metal alkoxide or hydride in an appropriate solvent such as the corresponding alcohol, benzene, toluene or xylenes. Typical reaction conditions include temperatures of about 60° to 90° C., pressures of about 100 to 500 kPa and reaction times of about 0.5 to 10 hours. The product can be recovered as the alkali-metal salt and isolated, for example, by filtration. Alternatively, the product can be first neutralized with an acid such as glacial acetic acid or dilute aqueous mineral acid; then isolated, for example, by filtration or extraction.

Step v) forms enantiomerically enriched II by reacting XI with about 0.9 to 1.5 equivalents of a hydroperoxide such as hydrogen peroxide and monoethers of hydrogen peroxide in the presence of about 0.001 to 1.5 equivalents of an optically-active amine base and optionally an inert solvent. Preferred monoethers of hydrogen peroxide include t-butylhydroperoxide, cumene hydroperoxide and combinations thereof. Suitable solvents include aliphatic hydrocarbons such as cyclohexane, aromatic hydrocarbons such as toluene, xylenes, ethylbenzene, mesitylene and cumene, halogenated hydrocarbons such as dichloromethane, dichloroethane and ortho-dichlorobenzene, ketones such as methylethylketone, methylisobutylketone and methylisopropylketone, esters such as methyl acetate, ethyl acetate, isopropyl acetate, and ethers such as diethyl ether and tetrahydrofuran. Aromatic hydrocarbon solvents are preferred. Typical reaction conditions include reaction temperatures in the range of about −5° to 50° C. and reaction times of about 2 hours to 8 days. The amine base is preferably a cinchona alkaloid or derivative thereof. Preferably, to produce II enriched with the (+) enantiomer (designated (+)II), the cinchona alkaloid is cinchonine, quinidine, the corresponding dihydro-derivatives of cinchonine or quinidine and any combination of the foregoing; wherein the chiral alkaloid has the [8-(R), 9-(S)] configuration. Formula II compounds enriched with the (−) enantiomer are obtained by employment of bases, such as cinchonidine, quinine and derivatives thereof, having the [8-(S), 9-(R)] configuration. The product can be recovered by standard methods including filtration, optionally following dilution with either a sufficient amount of aqueous acid to remove the catalyst or a non polar solvent such as hexanes. Alternatively, the product mixture can be diluted with a polar, water-immiscible solvent such as ethyl acetate, washed with aqueous acid to remove the catalyst, concentrated and crystallized. Optionally, II can be triturated or recrystallized with a suitable solvent, such as isopropyl acetate, to separate the pure enantiomer from the enriched enantiomeric mixture.

In a preferred embodiment, the solvent in step v is one in which the compound of Formula XI has a substantially greater solubility than the corresponding compound of Formula II. With such solvents, II will precipitate and can be recovered by filtration and the filtrate, containing any dissolved II, unreacted XI and catalyst, can be conveniently recycled to a subsequent batch. Preferably, the solvent is also water immiscible so the filtrate can be washed, prior to use in a subsequent batch, with aqueous base and/or water to reduce the amount of acidic impurities and water soluble byproducts. Recycle of the filtrate minimizes product loss and provides more efficient use of catalyst. Aromatic hydrocarbons such as xylenes are particularly preferred solvents for use in this manner, especially for the preparation of a compound such as Ia.

EXAMPLE 1

Illustration of steps a–d to form a compound of Formula I.

Step a: Formation of phenylmethyl[5-chloro-2.3-dihydro-2-hydroxy-2-(methoxycarbonvl)-1H-inden-1-ylidene] hydrazinecarboxylate (Compound IVa).

To a 1-L three-necked flask equipped with an overhead stirrer, thermometer, reflux condenser, and nitrogen inlet was charged 87 g (0.363 mol) of methyl 5-chloro-2,3-dihydro-2-hydroxy-1-oxo-1H-indene-2-carboxylate, 63.5 g (0.380 mol) of phenylmethyl hydrazinecarboxylate (from Lancaster Synthesis), 1.8 g (0.01 mol) of p-toluenesulfonic acid monohydrate, and 300 mL of methanol. The slurry was heated to reflux (67° C.), resulting in an orange solution from which the product gradually precipitated. After 14–16 h, the mixture was cooled to 5° C. and filtered. The filter cake was washed with 100 mL of cold methanol and dried at 60° C. under vacuum with nitrogen purge for 2 h to yield 135 g (96% based on the indene carboxylate) of IVa as a white crystalline solid. An analytical sample was prepared by recrystallization from acetonitrile, mp 187°–188° C.; $^1$H NMR (CDCl$_3$)δ3.23 (d, 1H, J=18 Hz), 3.48 (d, 1H, J=18 Hz), 3.7 (s, 3H), 4.58 (br s, 1H) 5.19 (br AB q, 2H), 7.18 (d, 1H), 7.25 (d of d, 1H), 7.45 (m, 5H), 7.75 (br d, 1H), 9.55 (br s, 1H). The product appears to be nearly exclusively the Z-(syn-) isomer.

Step b: Formation of 4a-methyl 2-(phenylmethyl)-7-chloroindeno[1.2-e][1,3,4]oxadiazine-2,4a(3H,5H)-dicarboxvlate (Compound Va).

To a dry 1-L three-necked flask equipped with an overhead stirrer, thermometer, reflux condenser, and nitrogen inlet was charged 42 g of diatomaceous earth, 500 mL of 1,2-dichloroethane, and 100 rnL of dimethoxymethane. Phosphorus pentoxide (42 g, 0.31 mol) was added under nitrogen with external cooling (20° C. bath) and the mixture was allowed to stir for 15 min at 20°–25° C. before adding 97 g (0.25 mol) of IVa in portions. The mixture was heated to 55°–60° C. for 2 h and then filtered. The filter cake was washed with two 100 mL portions of 1,2-dichloroethane and the combined filtrate was reduced in volume by distillation to about 150 mL. The pH was raised from about 1.5 to about 4 by the addition of about 5 g of NaOAc in 300 mL of methanol, and the residual dichloroethane was removed by distillation of about 150 mL of solvent. About 30 mL of water was then added, and the mixture was cooled to 5° C. and filtered. The filtered product was washed with 100 mL of cold methanol and suction-dried on the filter overnight to yield 89 g (89% based on IVa) of Va. An analytical sample was prepared by recrystallization from isopropanol, mp 122°–124° C.; IH NMR (CDCl$_3$) δ3.16 (d, 1H, J=16 Hz), 3.42 (d, 1H, J=16 Hz), 3.64 (s, 3H), 5.12 (d, 1H, J=10 Hz), 5.26 (AB q, 2H, J=12 Hz), 5.53 (br, d, 1H, J=10 Hz). 7.2–7.45 (m, 7H), 7.65 (d, 1H, J=9 Hz).

Step c: Formation of methyl 7-chloro-2,5-dihydroindeno[1,2-e][1,3,4]oxadiazine-4a(3H)-carboxylate (Compound VIa).

A 1-L three-neck flask equipped with magnetic stirrer, thermometer, pH probe, and gas inlet valve with a three-way stopcock was flushed with nitrogen and charged with 27.3 g (0.13 mol) of citric acid monohydrate, 100 mL of water, 10.4 g (0.13 mol) of 50% aqueous NaOH, 0.6 g of 5% palladium-on-carbon, 500 mL of methyl acetate, and 52.0 g (0.13 mol) of Va. The reaction vessel was purged with nitrogen and the mixture was stirred vigorously for about 3 h at 5°–10 ° C. while passing a stream of hydrogen subsurface. The reaction was monitored by HPLC for disappearance of Va; when the reaction was complete (about 4 h), the reaction vessel was purged with nitrogen and the palladium-on-carbon was filtered onto a pad of diatomaceous earth and rinsed with 50 mL of methyl acetate and 20 mL of water. The filtrate was separated, and the organic phase containing VIa was used directly in the next step. In a separate batch, the above procedure for Step c was repeated and VIa was isolated by removing about 400 mL of solvent by distillation, adding about 100 mL of hexanes and filtering and suction drying the crystallized product, mp 124°–127° C.; $^1$H NMR (CDCl$_3$) δ3.18 (d, 1H, J=17 Hz), 3.40 (d, 1H, J=17 Hz), 3.65 (d, 3H), 4.43 (d, 1H, J=7 Hz), 4.79 (d, 1H, J=7 Hz), 6.10 (br s, IH), 7.25 (m, 2H), 7.54 (d, 1H, J=8 Hz).

Step d: Formation of methyl 7-chloro-2.5-dihydro-2-[[(methoxycarbonyl)[4-(trifluoromethoxy)-phenyllamino]carbonvl]indeno[1.2-e] [1.3.4]oxadiazine4a(3H)-carboxvlate (Compound Ia).

To the organic phase from the Step c containing VIa was added aqueous saturated NaHCO$_3$ (140 g, about 0.15 mol), followed by 41 g (0.14 mol) of methyl (chlorocarbonyl)[4-(trifluoromethoxy)phenyl]carbamate (Compound VII) and the mixture was stirred for about 1 h at 10°–15° C. The organic phase was separated, dried (MgSO$_4$), concentrated under vacuum to remove about 400 ml of methyl acetate, and the residual solvent was exchanged by distillation with 300 mL of methanol until the head temperature reached 64° C. The mixture was cooled to 5° C. and the product was filtered, washed with 70 mL of cold methanol and suction-dried to yield 58 g of Ia (85% overall, based on Va from Step c), mp 139°–141° C.; $^1$H NMR (CDCl$_3$)δ 3.25 (d, 1H, J=16 Hz), 3.48 (d, 1H, J=16 Hz), 3.70 (s,3H), 3.71 (s,3H), 5.20 (d,1H, J=10 Hz), 5.69 (d, 1H, J=10 Hz), 7.2–7.4 (m, 6H), 7.50 (d, 1H, J=8 Hz).

EXAMPLE 2

Illustration of steps i-v to form a compound of Formula II.

Step i: Formation of 6-chloro-3.4-dihydro-2(1H)-naphthalene (Compound VIIIa).

To a flask was charged 34 g (0.20 mol) of 4-chlorophenylacetic acid (PCPA) and 150 mL of 1,2-dichloroethane. The suspension was stirred, 25 g (0.21 mol) of thionyl chloride was added and the resultant solution was heated at 80°–90° C. for 2–3 h. A distillation head was attached, and 25 mL of solvent was distilled in order to remove residual SO$_2$ and HCl. The pale orange solution of the acid chloride was cooled to −5° C., aluminum chloride (30 g, 0.22 mol) was charged at −5° to 0° C., and the distillation apparatus was replaced with a balloon. Ethylene gas (12 g, 0.43 mol) was charged to the balloon in portions, while maintaining the temperature at −5° to 0° C. The red solution was transferred gradually by cannula into 200 mL of 5° C. quench water at a rate to maintain the quench temperature at 20°–30° C. After the mixture was stirred for 1 h at 25° C., the lower organic layer containing VIIIa was separated and washed with 100 mL of 5% aqueous HCl.

Step ii: Formation of 2-carboxy-5-chlorobenzenepropanoic acid (Compound IXa).

The solution of VIIIa from the previous step was charged to a flask equipped with an overhead stirrer. Sodium acetate (16 g, 0.20 mol) was charged to the pot and the mixture was stirred at 25°–30° C. with cooling while 114 g (0.60 mol) of 32% peracetic acid was continuously added from a constant-addition funnel over 3–4 h. The mixture was allowed to stir an additional 20 h at 25° C. and then 300 mL of 0.8N HCl was added and the resulting slurry was cooled to 5° C. The mixture was filtered, washed with cold 5% aqueous NaHSO$_3$, water, suction-dried, and dried overnight in a vacuum oven at 50° C. and reduced pressure to afford 35–36 g (76–78% yield based on PCPA) of 99% pure IXa as a white crystalline solid, m.p. 156–158° C.

Step iii: Formation of methyl 5-chloro-2-(methoxycarbonyl)benzenepropanoate (Compound Xa).

To a flask equipped with a thermowatch and overhead stirrer was charged 45.7 g (0.200 mol) of IXa, 5 mL of methanol, and 100 mL of dimethyl carbonate. Sulfuric acid (1 g) was added, and the mixture was stirred under nitrogen at 85° C. for 20 h. The acid was neutralized with 3 g of 25% sodium methoxide solution and the bulk of the dimethyl carbonate (DMC) was distilled from the reaction flask. Methanol (100–200 mL) was added during distillation to form the methanol/DMC azeotrope (62° C.) to facilitate removal of the DMC which would otherwise distill at 90° C. The product from this step was carried into the next step without isolation.

Step iv: Formation of methyl 5-chloro-1-oxo-2,3-dihydroindene-2-carboxylate (Compound XIa).

After most of the DMC was removed, an additional 150 mL of methanol was added to the methanol solution of Xa from the previous step, followed by 47.5 g (0.22 mol) of 25% NaOMe in methanol. The solution was maintained at 70° C., and methanol was distilled to the minimum level required for efficient stirring. When the reaction was complete, the mixture was cooled to ambient temperature. Acetic acid (3 g, 0.05 mol), was added, followed by sufficient IN HCl to bring the pH to 5–6. The mixture was cooled to 5° C., filtered, and the crude solid was washed with water, then cold hexanes, affording 40–42 g (89–93% yield) of XIa as a beige solid, m.p. 80°–82° C.

Step v: Formation of (+)methyl 5-chloro-1.3-dihvdro-2-hydroxv-1-oxo-2H-indene-2-carboxvlate (Compound (+)IIa)

A mixture of 10.0 g of XIa, 17 mL (51 mmol) of a 3.0M t-butylhydroperoxide in iso-octane, 70 mL of isopropyl acetate and 0.2 g of cinchonine (Aldrich® Chemical Co.) was stirred at ambient temperature for 6 days. To the mixture was added about 100 mL of ethyl acetate, 30 mL of dilute aqueous sodium bisulfite and 20 mL of 2N HCl. The mixture was shaken and separated, and the organic extract was washed sequentially with water and brine. The solvent was removed under vacuum and the crude solid product was washed with hexane to afford 7.31 g of Ia (68% yield) having an enantiomeric ratio of 72% (+) to 28% (−) as determined by HPLC analysis using a chiral column. The (+) enriched Ia was recrystallized from isopropyl acetate to yield 4 to 5 g of the pure (+)IIa, m.p. 163°–165° C.; $[\alpha]_D^{25}$ +115.1° (CHCl$_3$, c=1.0); $^1$H NMR (CDCl$_3$)δ 3.21 (d, 1H, J=18 Hz), 3.67 (d, 1H, J=18 Hz), 3.72 (s,3H), 4.07 (s,1H), 7.38 (d of d, 1H, J=8 and 1 Hz), 7.47 (d,1H, J=1 Hz), and 7.70 (d,1H, J=8 Hz).

EXAMPLE 3

Illustration of an alternative operation of steps a-d starting from enantiomerically enriched IIa and forming enantiomerically enriched Ia.

Step a: Formation of (+)IVa

To a 1-L single-necked flask equipped with a Dean-Stark apparatus and a nitrogen inlet was added 75 g (0.312 mol) of (+)IIa (50% enantiomeric excess), 54.6 g (0.358 mol) of phenylmethyl hydrazinecarboxylate, 1.78 g (0.0094 mol) of p-toluenesulfonic acid monohydrate (Aldrich® Chemical Company), and 275 mL of 1,2-dichloroethane. The slurry was heated to reflux, resulting in an orange solution from 10 which the product gradually precipitated. The water phase collected in the Dean-Stark trap was removed. After 2 h, the mixture was cooled to room temperature. The reaction mixture was used directly in Step b.

Step b: Formation of (+)Va

To a 2-L three-necked flask equipped with an overhead stirrer, thermometer, reflux condenser, and nitrogen inlet was added 88.5 g of diatomaceous earth (Celite®) and 300 mL of 1,2-dichloroethane. Phosphorus pentoxide (88.5 g, 0.623 mol) was added followed by 120 mL of dimethoxymethane. The slurry of (+)IVa in 1,2-dichloroethane from step a was then added. The mixture was heated to 35°–40° C. for 5 h, and then cooled to 30° C. and filtered. The filter cake was washed with 135 mL of 1,2-dichloroethane and the combined filtrate was distilled to minimum volume. Methanol was added and the distillation was continued. When all the 1,2-dichloroethane was removed and approximately 500 mL of methanol remained in the pot, the distillation was stopped and the pot was cooled to 45° C. The product began to precipitate, and 120 mL of water was added. Cooling was continued to 20° C. The mixture was filtered, and the filter cake was washed with 370 mL of 3:1 methanol/water. The solid was dried overnight under vacuum at 80° C. to yield 100.5 g (80.5% for 2 steps) of (+)Va. The IH NMR spectrum matched that obtained for Va in Example 1. Purity was 99.3% by HPLC. Analysis by chiral HPLC indicated 43% enantiomeric excess of the (+) enantiomer.

Step c: Formation of compound (+)VIa.

A 500 mL 3-neck flask equipped with magnetic stirrer, thermometer and gas inlet valve with 3-way stopcock was flushed with nitrogen and charged with 50 mL of methyl acetate, 50 mL of 0.5M sodium di-hydrogen phosphate buffer solution (pH 3.5) and 0.2 g of 50% water-wet 5% palladium-on-carbon. The two-phase suspension was stirred at ambient temperature for 0.5 h. In a separate flask, 10 g (0.025 mole) of (+)Va was added to 50 mL of methyl acetate under nitrogen, heated to 35° C. and stirred until dissolved. The solution of (+)Va was added to the Pd catalyst suspension and the mixture was cooled to 10° C. The reaction vessel was evacuated and the mixture was stirred vigorously at 10° C. while passing in a stream of hydrogen subsurface. The reaction was monitored for disappearance of (+)Va by TLC and GC. When the reaction was complete (about 1.5 h), the reaction vessel was evacuated and purged with nitrogen; the reaction mixture was filtered through a pad of diatomaceous earth and the filter pad was washed with an additional 20 mL of methyl acetate. The liquid phases were separated and the methyl acetate phase containing (+)VIa was carried directly on to step d.

Step d: Formation of (+)Ia

The methyl acetate solution from step c containing (+)VIa was added to a solution of 3 g of NaHCO$_3$ in 38 mL of water. The mixture was cooled to 10° C. under nitrogen and 7.43 g (0.025 mole) of VII was added in one portion. The reaction was stirred at 10° C. for 1 h. The methyl acetate phase was separated and concentrated under vacuum to remove about 100 mL of solvent. Methanol, 50 mL, was added and the slurry was re-evaporated to remove the remaining methanol as the methyl acetate/methanol azeotrope. A final 50 mL of methanol was added and the suspension was heated to reflux. Diatomaceous earth (0.4 g) was added as heating was continued and then 17 mL of water was added dropwise. The resulting slurry was cooled, filtered, washed with 33 mL of 2:1 methanol/water, and vacuum dried to afford 11.16 g of enriched (+)Ia (78% overall yield for steps c and d based on Va). Analysis by chiral HPLC indicated 42% excess of the (+) enantiomer.

EXAMPLE 4

Illustration of an alternative operation of steps c and d.

Step c: Formation of VIa.

A 1-L 3-neck flask equipped with magnetic stirrer, thermometer, and gas inlet valve with three-way stopcock was flushed with nitrogen and charged with 580 mL of methyl acetate, 0.164 g sodium acetate (2 mol %), and 0.8 g of 5% palladium-on-carbon catalyst. Approximately 200 mL of solvent was removed by distillation and the resulting dry solvent/catalyst suspension was allowed to cool to 50° C. and 40.0 g (0.1 mole) of Va was added in one portion. The mixture was stirred to dissolve Va and then cooled to ambient temperature. The reaction vessel was purged with nitrogen then the mixture was stirred vigorously at ambient temperature as a stream of hydrogen was admitted subsurface. The reaction was monitored for disappearance of Va. When the reaction was complete (about 3.0 h), the reaction vessel was evacuated and purged with nitrogen; the palladium-on-carbon was filtered onto a pad of diatomaceous earth and rinsed with 50 mL of dry methyl acetate. The filtrate was used directly in step d.

Step d: Formation of Ia.

The methyl acetate solution from Step c containing VIa was combined with a solution of 12 g of NaHCO$_3$ in 150 iL of water. The mixture was cooled to 10° C. under nitrogen and 29.7 g (0.1 mole) of compound VII was added in portions over 0.5 h; the mixture was stirred for about an additional hour at 10°–15° C. The methyl acetate phase was then separated and concentrated under vacuum to remove about 400 mL of solvent. Methanol (50 mL) was added and the solvent again removed in vacuo. 70% aqueous methanol (100 g) was then added and the mixture was stirred for 45 minutes with cooling from an ice bath. The product was filtered, washed with 25 mL of cold 70% aqueous methanol, and vacuum dried to yield 51 g (86% overall yield from Va based on 88.9% HPLC assay), mp 135°–138° C.

EXAMPLE 5

Illustration of an alternative operation of step v.
Step v: Formation of compound (+)IIa.

A suspension of 11.25 g (50 mmol) of Va, 70 mL of mixed xylenes, and 1.4 g (4.8 mmol) of cinchonine (Aldrich® Chemical Co.) was stirred under nitrogen and 7.0 g (70 mmol) of 90% aqueous t-butyl hydroperoxide (Aldrich® Chemical Co.) was added. The resulting solution was allowed to stir at room temperature for 24 hours during which time the product began to crystallize. The reaction mixture was then diluted with 100 mL of ethyl acetate and washed successively with two 50 mL portions of saturated aqueous sodium bicarbonate, 50 mL of 1N aqueous hydrochloric acid, and 50 mL of saturated aqueous sodium bisulfite. The organic phase was dried over magnesium sulfate and the solvent removed under reduced pressure to give 10.6 g of enriched (+)IIa (86% purity, 76% yield based on Va). Analysis by chiral HPLC indicated 45% enantiomeric excess of the (+) enantiomer.

EXAMPLE 6

Illustration of an alternative operation of step b.
Step b: Formation of Compound Va.

To a dry 500 mL 4-neck flask equipped with a magnetic stirrer, thermometer, and two gas inlets was charged 49.9 g (0.128 mol) of IVa and 250 mL of diethoxymethane. The mixture was cooled to −10° C. and the reaction vessel was evacuated (~24 cm Hg pressure). Sulfur trioxide gas was admitted to the cooled reaction vessel at a rate such that temperature of the reaction mixture was maintained between −10° C. to 0° C. When the addition was complete, nitrogen was admitted to release the vacuum. The mixture was allowed to warm to room temperature, stirred for 4.75 h, added to 50 mL of water at room temperature with good stirring and stirred for an additional 2 h. The mixture was filtered and the organic phase from the filtrate was separated and evaporated. The residue was dissolved in 125 mL of methanol and combined with the solid from the filtration. To this slurry was added 125 mL of water dropwise after which the mixture was stirred for 1.5 h, then filtered. The filter cake was dried under vacuum at room temperature to give 46.3 g (90% based on IVa) of Va. A small portion of product was recrystallized from methanol to afford a sample whose mp and $^1$H NMR spectrum matched that of Va obtained in Example 1, step b.

EXAMPLE 7

Preparation of methyl (chlorocarbonyl)[4-(trifluoromethoxy)phenyl]carbamate (Compound VII).

In a first reaction flask, 70.5 g (0.30 mole) of methyl 4-(trifluoromethoxy)phenyl carbamate is dissolved in 700 mL of dichloromethane. Then 14.0 g of 60% sodium hydride (0.35 mole) in mineral oil is added followed by 60 mL glyme (ethylene glycol dimethyl ether) within 15 min. There is exothermic reaction and the temperature of the reaction mixture increases to slightly above that of the ambient room temperature. The reaction mixture is stirred overnight (ca. 16 h) without external heating. In a second reaction flask equipped with a distillation column, 120 g (1.2 mole) of phosgene is dissolved in 300 ml dichloromethane which is cooled to 5°–10C. The reaction mixture from the first flask, a thick slurry, is slowly added to the second flask containing the phosgene solution at 5°–10C. After addition is complete, excess phosgene is removed by distillation until the head temperature indicates only dichloromethane is coming overhead. Distillation is stopped, and the reaction mixture is cooled to about 0°C. Ice water, 200 mL, is added to dissolve the byproduct sodium chloride. The dichloromethane layer is separated from the aqeuous layer, filtered and dried with $MgSO_4$. The dried dichloromethane solution, c which contains compound VII, is then distilled to take off the dichloromethane and in exchange, hexane, 400 mL total, is added (solvent exchange procedure). When the dichloromethane is removed and the hexane begins to distill, distillation is stopped. The hexane solution is then cooled to 5° C. whereupon VII is precipitated (seeding may be required), recovered by filtration, washed with additional cold hexane and dried. Yield is typically about 94% for 97–98% pure VII, m.p. 97–99° C. $^1$H NMR (CDCl$_3$)δ 3.80(S,3), 7.29 (S,4).

We claim:

1. A method for preparing a compound of Formula I which is racemic or enantiomerically enriched at chiral center*

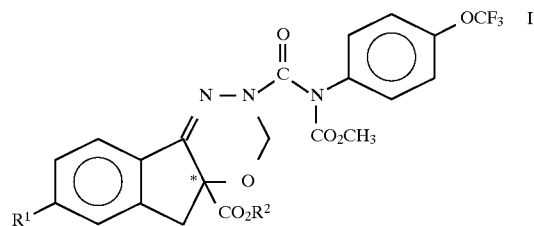

wherein:

$R^1$ is F, Cl, or $C_1$–$C_3$ fluoroalkoxy, and
$R^2$ is $C_1$–$C_3$ alkyl, comprising:
(a) reacting a compound of Formula II, optionally enantiomerically enriched at *

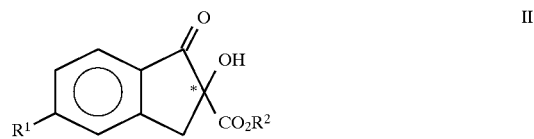

with the compound of Formula III in the presence of acid catalyst
to form a compound of Formula IV

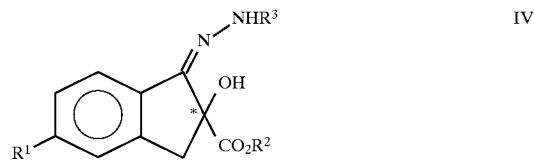

wherein:

$R^3$ is the protecting group $CO_2CH_2(C_6H_5)$;
(b) reacting the compound of Formula IV with di($C_1$–$C_3$ alkoxy)methane in the presence of a Lewis acid to form a compound of Formula V

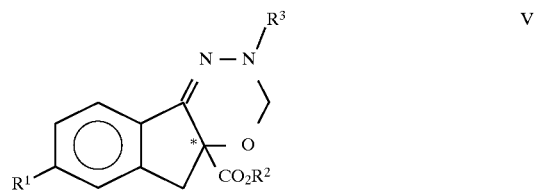

(c) hydrogenating the compound of Formula V to form a compound of Formula VI 5,869,657

15

![Formula VI: indanone hydrazone structure with R¹, CO₂R², N-NH]

(d) reacting the compound of Formula VI with the compound of Formula VII

![Formula VII: Cl-C(=O)-N(CO₂CH₃)-C₆H₄-OCF₃]

to form a compound of Formula I having substantially the same absolute configuration as the compound of Formula II.

2. A method for making a compound of Formula V:

![Formula V structure]

comprising
(a) reacting a compound of Formula II, optionally enantiomerically enriched at *, ![Formula II structure]

with the compound of Formula III in the presence of acid catalyst
to form a compound of Formula IV ![Formula IV structure]

wherein:
R¹ is F, Cl, or $C_{1-C_3}$ fluoroalkoxy,
R² is $C_1$–$C_3$ alkyl, and
R³ is the protecting group $CO_2CH_2(C_6H_5)$; and
(b) reacting the compound of Formula IV with di($C_1$–$C_3$ alkoxy)methane in the presence of a Lewis acid.

3. A method for making a compound of Formula VI:

![Formula VI structure]

comprising hydrogenating the compound of Formula V of the formula

16

![Formula V structure]

4. A method for making a compound of Formula VI:

![Formula VI structure]

comprising reacting a compound of Formula IV

![Formula IV structure]

wherein:
R¹ is F, Cl, or $C_1$–$C_3$ fluoroalkoxy,
R² is $C_1$–$C_3$ alkyl, and
R³ is the protecting group $CO_2CH_2(C_6H_5)$;
with di(Cl-$C_3$ alkoxy)methane in the presence of a Lewis acid, to form a compound of Formula V ![Formula V structure]

and hydrogenating the compound of Formula V.

5. A method for making a compound of Formula I

![Formula I structure]

wherein:
R¹ is F, Cl, or $C_1$–$C_3$ fluoroalkoxy, and
R² is $C_1$–$C_3$ alkyl,
comprising hydrogenating a compound of Formula V ![Formula V structure]

wherein:
R³ is the protecting CO₂CH₂(C₆H₅); to form a compound of Formula VI
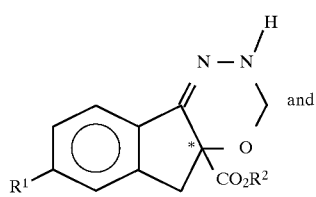
VI
and
reacting the compound of Formula VI with a compound of Formula VII
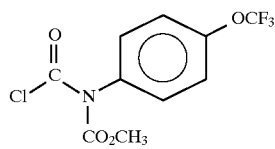
VII
6. A racemic or enantiomerically enriched compound of the formula
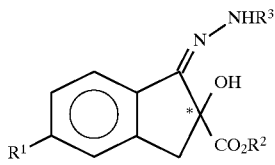
and
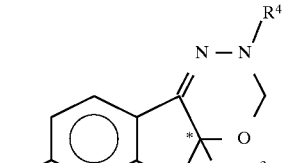
wherein:
R¹ is F, Cl, or C₁–C₃ fluoroalkoxy, R² is C₁–C₃ alkyl, and R⁴ is CO₂CH₂(C₆H₅).
* * * * *

UNITED STATES PATENT AND TRADEMARK OFFICE
CERTIFICATE OF CORRECTION

PATENT NO. : 5,869,657
DATED : February 9, 1999
INVENTOR(S) : Gary David Annis; Stephen Frederick McCann; Rafael Shapiro It is certified that error appears in the above-identified patent and that said Letters Patent is hereby corrected as shown below:

Col. 3, line 66: "C$_1$-C3 alkyl" should be "C$_1$-C$_3$ alkyl".
Col. 5, lines 19 and 20: various "SO3" should read "SO$_3$".
Col. 6, line 53: "1to 4" should read "1 to 4".
Col. 9, line 43: "...-phenyllamino]" should read "...-phenyl]amino]".
Col. 10, line 26: "IICI" should read "HCl".
Col. 10, line 64-65: "3.0M t-butylhydroperoxide" should read "3.0M solution of t-butylhydroperoxide".
Col. 11, line 6: "Ia" should read "IIa".
Col. 11, line 27: extraneous "10" at the end of line.
Col. 12, line 51: "150 iL" should read "150 mL".
Col. 14, line 3: extraneous "c" before "which".
Col. 14, line 41 (Claim 1): The following structure of Formula III is missing after line 41.

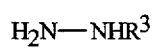

III

Col. 15, line 41 (Claim 2): The following structure of Formula III is missing after line 41.

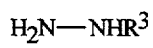

III

Col. 15, line 51 (Claim 2): "C$_{1-C3}$" should be "C$_1$-C$_3$".

UNITED STATES PATENT AND TRADEMARK OFFICE
CERTIFICATE OF CORRECTION

PATENT NO. : 5,869,657
DATED : February 9, 1999
INVENTOR(S) : Gary David Annis; Stephen Frederick McCann; Rafael Shapiro It is certified that error appears in the above-identified patent and that said Letters Patent is hereby corrected as shown below:

Col. 16, line 8 (Claim 3): The definition of the variables is missing. Please insert after the structure V "wherein:

$R^1$ is F, Cl, or $C_1$-$C_3$ fluoroalkoxy, $R^2$ is $C_1$-$C_3$ alkyl, and $R^3$ is the protecting group $CO_2CH_2(C_6H_5)$."

Col. 16, line 9 (Claim 4): "Amethod" should read "A method".
Col. 16, line 32 (Claim 4): The word "di(CI-C3 alkoxy)methane" should read "di($C_1$-$C_3$ alkoxy)methane".

Col. 17, line 2 (Claim 5): The word "group" should be inserted after "protecting".
Col. 18, line 1 (Claim 6): The first structure and "and" should be deleted.

Signed and Sealed this

Twenty-ninth Day of August, 2000

Attest:

Q. TODD DICKINSON

*Attesting Officer*          *Director of Patents and Trademarks*